United States Patent [19]

Bazell et al.

[11] 4,444,188

[45] Apr. 24, 1984

[54] BALLOON CATHETER

[76] Inventors: Seymour Bazell, 9235 N. Latrobe, Skokie, Ill. 60077; Edward M. Goldberg, 225 Maple Hill Rd., Glencoe, Ill. 60022

[21] Appl. No.: 285,781

[22] Filed: Jul. 22, 1981

Related U.S. Application Data

[63] Continuation-in-part of Ser. No. 178,305, Aug. 15, 1980, Pat. No. 4,351,341.

[51] Int. Cl.³ ............................................. A61M 25/00
[52] U.S. Cl. .................................. 128/348.1; 604/95; 604/97; 604/103; 128/344
[58] Field of Search ............... 128/325, 344, 348–350, 128/1 D; 604/95–103, 282

[56] References Cited

U.S. PATENT DOCUMENTS

| 3,480,017 | 11/1969 | Shute | 128/344 |
| 3,757,768 | 9/1973 | Kline | 128/348 X |
| 3,837,347 | 9/1974 | Tower | 128/344 X |
| 3,978,863 | 9/1976 | Fettel et al. | 128/349 B X |
| 4,205,691 | 6/1980 | Patel | 128/349 B X |
| 4,261,339 | 4/1981 | Hanson et al. | 128/1 D |
| 4,307,722 | 12/1981 | Evans | 128/344 |

FOREIGN PATENT DOCUMENTS

512456 9/1939 United Kingdom ................ 128/344

Primary Examiner—Dalton L. Truluck
Attorney, Agent, or Firm—Norman Lettvin

[57] ABSTRACT

The disclosed balloon catheter includes a proximal catheter segment, a distal catheter segment, and an inflatable balloon member secured to and disposed between the proximal and distal catheter segments. A tension member is secured to the distal catheter segment and passes through the lumen of a coil spring included in the proximal catheter segment, such that the tension member is free to slide within the coil spring. A stop member is secured to the proximal end of the tension member to limit the sliding movement of the tension member inside the proximal catheter segment. The disclosed structure permits the balloon member to stretch both axially and circumferentially as it inflates, thereby improving the concentricity of the resulting balloon. In addition, in the preferred embodiment the stop member is positioned on the tension member such that the tension member is free to slide further in the coil spring after the balloon member has been inflated to its normal inflated state, thereby providing protection against overpressures in the balloon member.

10 Claims, 17 Drawing Figures

BALLOON CATHETER

BACKGROUND OF THE INVENTION

This application is a continuation-in-part of U.S. patent application Ser. No. 178,305, filed Aug. 15, 1980, now U.S. Pat. No. 4,351,341, issued 9-23-1982.

The present invention relates to an improved ballon catheter for insertion in a body passage.

Balloon catheters of various types are known to the art. For example, U.S. Pat. No. 3,435,826 (Fogarty) and U.S. Pat. No. 3,467,101 (Fogarty, et al.) disclose two types of embolectomy catheters used to remove blood clots from blood vessels. As explained in the earlier Fogarty patent, such a catheter is used by first inserting it through an incision into a blood vessel and moving the deflated balloon to a point beyond the clot, then inflating the balloon on the remote side of the clot and withdrawing the catheter. The balloon acts as a drag to push the clot ahead of it until it reaches the incision where it can be readily withdrawn.

The use of such balloon catheters brings with it certain dangers. If excessive transmitted wall pressures and excessive shear stresses are applied to the vessel wall in withdrawing the catheter from the blood vessel, the blood vessel can be seriously damaged or even ruptured. Furthermore, if the balloon or other parts of the catheter fragment while in use, portions of the catheter can become lost in the vessel, thereby creating the danger of obstructions in the vascular system.

SUMMARY OF THE INVENTION

The present invention is directed to an improved balloon catheter which provides important safety advantages over catheters of the prior art.

According to one aspect of this invention, a catheter includes a balloon mounted on an elongated support structure which is elongatable in response to an applied stretching force greater than a first value. This first value is chosen such that the support structure elongates perceptibly when an excessive stretching force is applied to the support structure in pulling the balloon through a body passage, thereby providing a tactile indication to a user of the catheter that an excessive stretching force is being applied.

Preferably, the support structure includes a coil spring covered with an extensible sheath, and the coil spring is tightly wound with adjacent coils in contact with each other such that elongation of the support structure is imperceptible for stretching forces smaller than a threshold value, less than or equal to the first value. However, when stretching forces greater than the first value are applied, the support structure elongates perceptibly. By setting the first value at a point greater than that needed to pull the balloon safely through the body passage but less than that at which damage is done to the body passage, the user of the catheter is given a tactile signal whenever he applies an excessive stretching force to the catheter. In addition, the support structure is preferably constructed to temporarily receive fluid and relieve pressure from the balloon when the support structure elongates. This reduces balloon volume and pressure, thereby further reducing the danger of damaging the body passage in the event an excessive stretching force is applied to the catheter.

According to a second aspect of the invention, a balloon catheter is provided with a balloon and means for receiving and storing fluid from the balloon to temporarily reduce the volume of the balloon when the fluid pressure in the balloon exceeds a predetermined value. In this way strain on the balloon, as well as the pressure exerted by the balloon on the body passage, are automatically reduced when excessive pressures are created in pulling the balloon through a body passage.

Preferably, the receiving means includes a strain relief collar mounted adjacent the balloon. This relief collar moves into an extended position in response to excessive fluid pressure or tension on the balloon to receive fluid from the balloon. Furthermore, the preferred relief collar provides further advantages in terms of improved reliability of the bond between the balloon and the catheter.

According to a third aspect of the invention, a balloon catheter is provided with a chamber in fluid communication with the balloon, which chamber is provided with at least one flexible, deformable wall. This chamber is adapted to be manipulated by digital pressure of a user to provide precise and direct control of the inflation pressure of the balloon. Preferably, the chamber includes an elastomeric chamber included as an integral part of the balloon catheter and sized to fit between the thumb and an opposed finger of the user such that the thumb of the user bears directly on the deformable wall of the chamber.

According to a fourth aspect of the invention, the balloon and the outer layer of the support structure are formed of silicone rubber, which has a reduced tendency to fragment if it ruptures. Furthermore, silicone rubber is extensible, it does not soften excessively at body temperature, and it provides a balloon which conforms readily to the contours of the body passage. If excessive stretching forces are applied in withdrawing the silicone rubber balloon, it tends to extend longitudinally in a pear shaped configuration, further limiting shear stress and the concomitant danger of vessel damage. Preferably, the balloon is directly bonded to the catheter rather than being held by means of ties, because ties and the balloon can become lost in the body passage if they separate from the catheter in use.

According to a fifth aspect of this invention a balloon catheter for insertion in a body passage is provided which comprises a proximal catheter segment, a distal catheter segment, and an inflatable balloon member secured to and disposed between the proximal and distal catheter segments, and sized to fit within the body passage. Means are provided for coupling the proximal catheter segment to the distal catheter segment such that the separation therebetween, and therefore the length of the balloon member in the direction of the catheter, increases automatically under certain conditions.

Preferably, the coupling means allows the length of the balloon member to increase automatically when external pressures are applied to the inflated balloon member. This feature of the invention brings with it the important advantage that when the balloon catheter is being pulled through a body passage, and the inflated balloon member encounters a restricted portion of the body passage, the coupling means acts to allow the balloon member to elongate and thereby to reduce the effective diameter of the balloon member. In this way excessive and damaging extension of the body passage is significantly reduced.

In addition, in the preferred embodiment of this invention, the coupling means allows the separation between the proximal and distal catheter segments, and therefore the length of the balloon member in the direction of the catheter, to increase automatically as the balloon member inflates. In this way, the balloon member is caused to stretch in both the axial and the circumferential directions as the balloon member inflates. It has been found that this bi-directional stretching of the balloon member tends to cause the balloon member to inflate into a more concentric configuration with respect to the proximal and distal catheter segments.

A further advantage of this preferred embodiment is that it tends to reduce relative movement between the balloon and the blood vessel due to heart pumping. Because the distal end of the catheter is not inextensibly tied to the proximal end of the catheter, relative axial movement between the balloon and the proximal end of the catheter is possible. Thus, when the catheter is inserted in a vessel, inflated, and then allowed to remain in place, the distal end of the catheter and the balloon are free to move in rhythm with the vessel, even though the proximal end of the catheter is not. In this manner, relative movement, and therefore abrasion, between the balloon and the vessel wall are minimized, thereby reducing damage to the vessel wall as well as the danger of balloon rupture due to abrasive damage.

In the preferred embodiment described below, the proximal catheter segment includes a coil spring, and the coupling means includes a flexible wire which is secured to the distal catheter segment and is slidably disposed within the lumen of the coil spring of the proximal catheter segment. Means such as a stop member are provided to limit the sliding movement of this wire within the coil spring of the proximal catheter segment.

The invention, together with further objects and attendant advantages, will be best understood by reference to the following detailed description taken in conjunction with the accompanying drawings.

BRIEF DESCRIPTION OF THE DRAWINGS

FIG. 10b is a partial sectional view of a portion of the proximal part of the embodiment of FIG. 10a, showing the position of component parts when the balloon member is deflated as shown in FIG. 10a.

FIG. 11 is a sectional view taken along line 11—11 of FIG. 10a.

FIG. 12b is a partial sectional view corresponding to FIG. 10b, showing the position of component parts of the proximal portion of the catheter of FIG. 10b when the balloon member is inflated as shown in FIG. 12a.

DETAILED DESCRIPTION OF THE PRESENTLY PREFERRED EMBODIMENTS

Figures 1, 2:
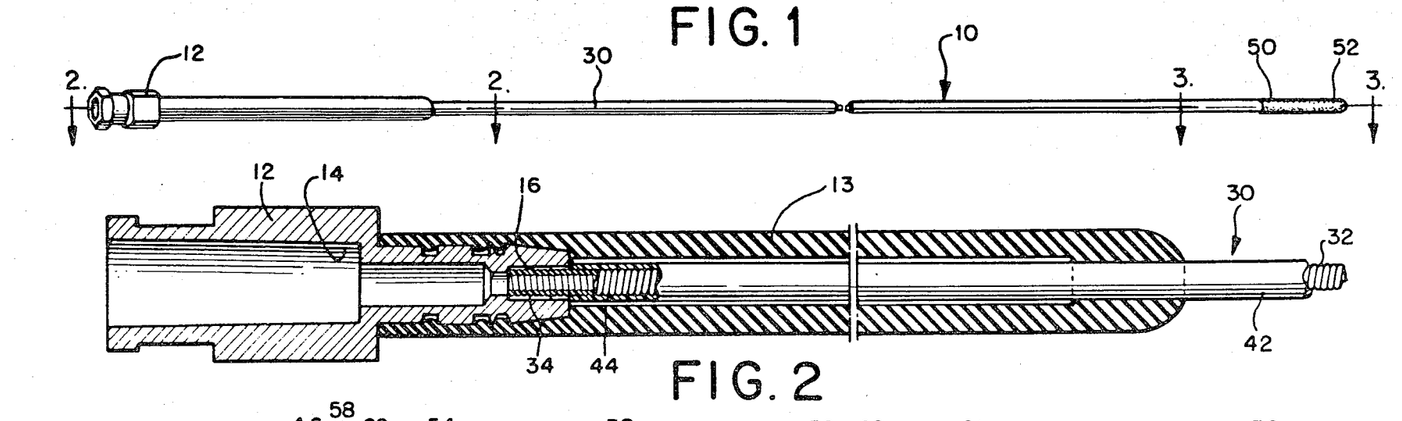
FIG. 1 is a perspective view of a first preferred embodiment of the balloon catheter of this invention.
FIG. 2 is a cross-sectional view of the luer portion of the balloon catheter of FIG. 1 taken along line 2—2 of FIG. 1.

Referring now to the drawings, FIG. 1 provides an overall view of a first preferred embodiment of the balloon catheter of this invention, which is indicated generally by the reference numeral 10. This catheter 10 is made up of three major components: a luer 12, a support structure 30, and a balloon tip assembly 50,52. Each of these major components will be described in detail.

As shown in FIG. 2, the luer 12 is a conventional syringe luer used to couple the balloon catheter 10 to a syringe (not shown) used to inflate the balloon 50. In this embodiment, the luer 12 is a metal adaptor No. 3084 L/609, marketed by Becton, Dickinson & Co. of Rutherford, N.J. This luer 12 includes a syringe receiving bore 14 sized to securely attach to the projecting end of a syringe, and a spring receiving bore 16. The spring receiving bore 16 is preferably swaged to achieve an internal diameter of 0.039 inches.

Figure 3:
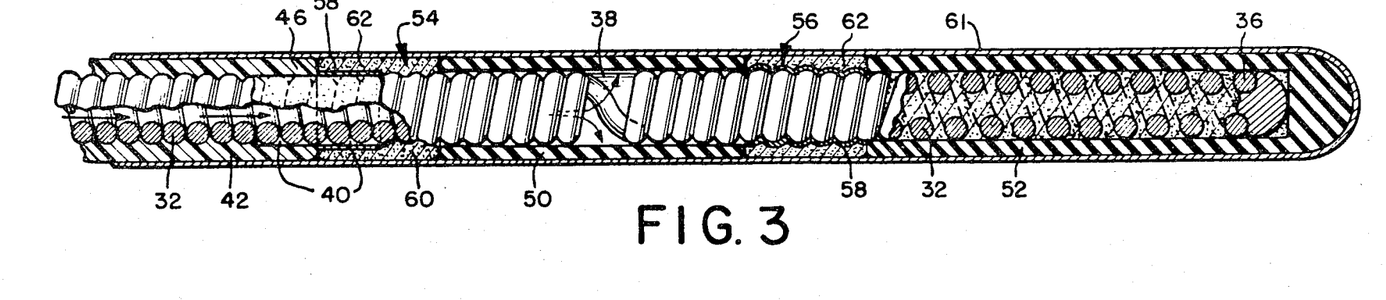
FIG. 3 is a cross-sectional view of the tip portion of the balloon catheter of FIG. 1 taken along line 3—3 of FIG. 1, showing the balloon in its deflated state.

The support structure 30 includes an internal coil spring 32 and an external sheath 42. The coil spring 32 includes a proximal end 34 which is inserted in the spring receiving bore 16 of the luer 12 and is soldered, swaged or screwed in place so as to securely attach the coil spring 32 to the luer 12. A support tube 13 of silicone rubber surrounds a portion of the luer 12 and the adjacent portion of the support structure. Furthermore, the coil spring 32 defines a distal end 36 which is soldered or welded to form a rounded end, as shown in FIG. 3. Preferably, the coil spring 32 has an outer diameter of 0.040 inches and is formed from closely spaced coils of stainless steel type 304, and is made of wire having a cross-sectional diameter of 0.011 inches. Throughout the length of the coil spring 32, the coils are in close contact with one another, except that at one point approximately 23/64 of an inch from the distal end 36, where the coils are spread as shown at reference numeral 38 of FIG. 3 and at the distal end of the spring 32. In addition, a number of coils of the spring 32 spread over a distance of about ⅛ inch are bonded together with a solder bond 40, also as shown in FIG. 3.

The coil spring 32 is covered with a elongatable sheath 42 in the region between the luer 12 and the solder bond 40. Preferably, this sheath is formed of silicone rubber tubing having an outside diameter (before it is assembled with the coil spring 32) of 0.052 inches. In this preferred embodiment the wall thickness of the sheath 42 is 0.013 inches, and the wall thickness is uniform to within one-thousandth of an inch. Preferably, insertion depth gauge marks at ten centimeter intervals are applied to the sheath 42. The sheath 42 is placed on the coil spring 32 by first expanding the silicone rubber of the sheath 42 with toluene. After the sheath 42 has been expanded it is then placed over the spring 32 and is then allowed to dry and shrink in place on the spring 32. The sheath 42 includes a proximal end 44 adjacent the luer 12 and a distal end 46 adjacent the balloon 50.

The distal end 36 of the spring 32 is covered with a balloon 50 and a tip section 52. Preferably the balloon 50 is bonded directly to the distal end 46 of the sheath 42 in a bonding region 54, and the tip section 52 is bonded directly to the balloon 50 in a bonding region 56. The structure of these bonding regions 54, 56 will be discussed in detail below. The tip section 52 is bonded to the spring 32 by means of a silicone rubber adhesive which fills the lumen of the spring 32 and all other space within the tip section 52. Preferably the tip section 52 is molded to a predetermined shape. This molding provides uniformity of size and wall thickness of the tip section 52, and allows the tip section to be preformed into the desired shape.

Preferably, the balloon 50 is approximately 5/32 of an inch in length, is formed of silicone rubber, and has a rest state diameter prior to assembly of 0.052 inches. The wall thickness of the balloon 50 is 0.010 inches, and the wall thickness is uniform to within 5/10,000 of an inch or less. The tip section 52 is also formed of silicone rubber in this preferred embodiment. The length of the tip section is about one quarter of an inch in length, and it has a rest diameter (prior to assembly) of 0.050 inches. The wall thickness of the tip section is preferably 0.005 inches. When assembled, the balloon 50 is centered on the spread section 38 of the coil spring 32.

Figure 4:
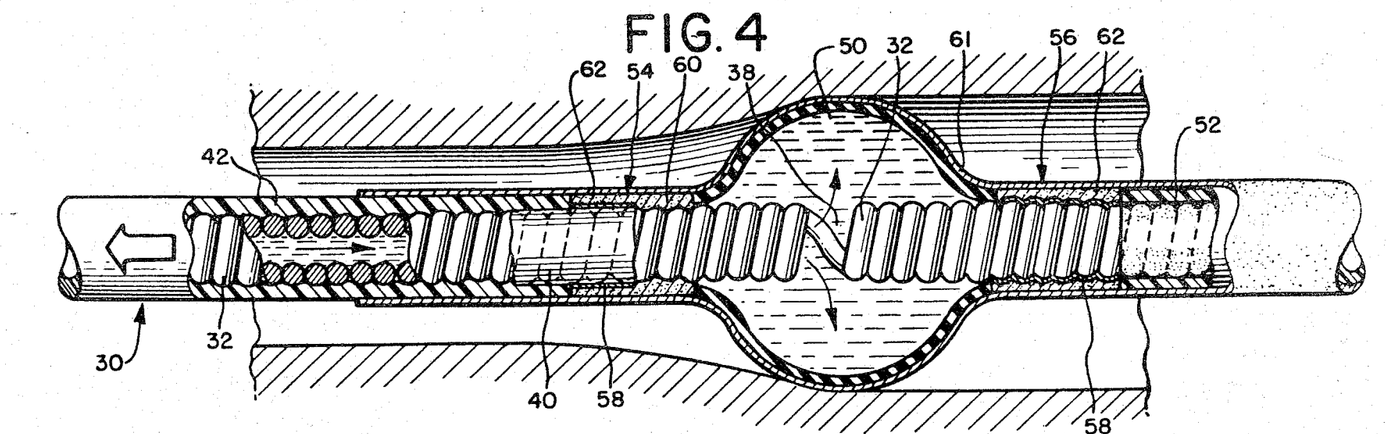
FIG. 4 is a cross-sectional view of the tip portion of the balloon catheter of FIG. 1, showing the balloon in its inflated state.
Figure 5:
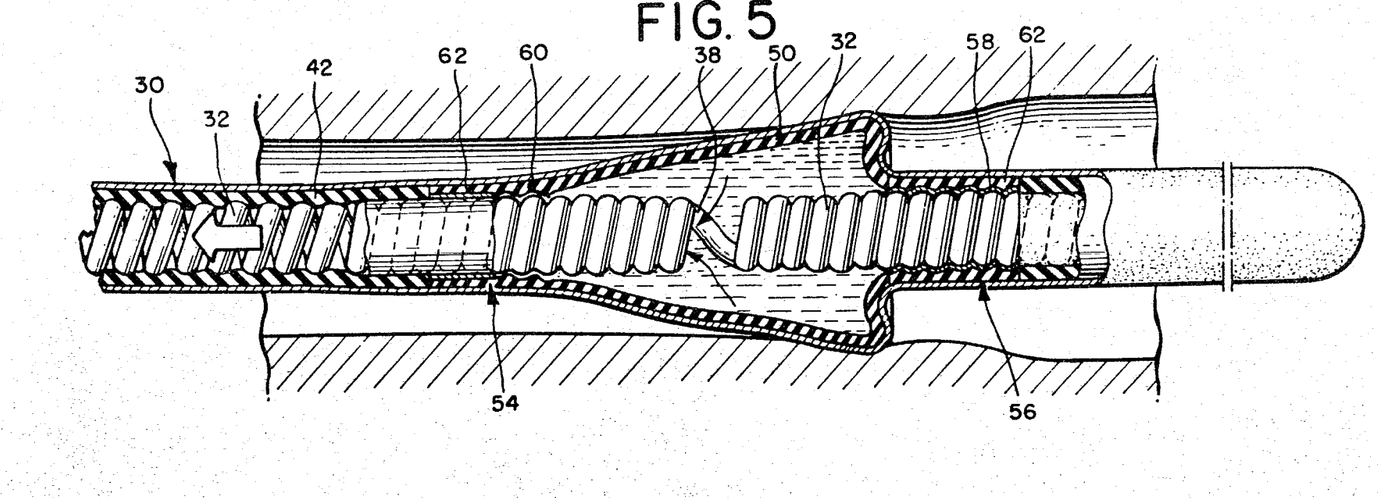
FIG. 5 is a cross-sectional view of the tip portion of the balloon catheter of FIG. 1, showing the balloon inflated, elongated and pear shaped as it is pulled through a body passage.

The bonding regions 54 and 56 as shown in FIGS. 3-5, are each about 1/16 of an inch in length in this preferred embodiment. The bonding region 54 includes a strain relief collar 60 adjacent the balloon 50, and a secured section 62 adjacent the sheath 42. A coating of a primer 58 is applied between the secured section 62 and the coil spring 32 in order to insure that the secured section 62 adheres firmly to the coil spring 32. Both the strain relief collar 60 and the secured section 62 are formed from silicone rubber adhesive in this preferred embodiment. In addition, the bonding region 56 is also preferably formed of silicone rubber applied over a coating of a primer 58 to bond the bonding region 56 to the spring 32. Thus, in this preferred embodiment, the sheath 42, the bonding regions 54,56, the balloon 50, and the tip section 52 are all formed of silicone rubber. Preferably, the bonding regions 54,56 are bonded to the silicone rubber sheath 42, balloon 50 and tip section 52 in order to securely bind each of the component parts of the balloon catheter into a single unit. In this way, the use of windings is avoided and an integral balloon catheter is provided. After the balloon catheter 10 is fully assembled, the distal end of the catheter 10 is dip coated with two coats of silicone rubber 61. This dip coating covers the distal ¾ of an inch of the catheter.

The dimensions of the preferred embodiment described above are appropriate for a size 4 (French) catheter. Of course, it should be understood that these dimensions are merely illustrative, and are not to be taken as limiting the scope of the invention, which is suitable for use in a wide range of catheter sizes. For example, the present invention can be embodied in catheters ranging as small as size 2 (French) or even smaller, and as large as size 7 (French), or even larger. The dimensions described above can be appropriately scaled for a wide range of catheter sizes.

In this preferred embodiment, the support tube 13, the sheath 42, the balloon 50 and the tip section 52 are all formed of food grade silicone rubbers having the desired durometers and extensability. Silicone rubbers marketed by Dow Corning, General Electric and Stauffer-Waker-Stauffer are blended to produce compounds with the desired physical characteristics. The primer 58 is preferably primer No. 608 marketed by Hughson Chemical Division of Lord Chemical Corp. The adhesive used to secure the tip section 52 to the spring 32 and to form the bonding regions 54 is preferably adhesive No. 951 marketed by Stauffer-Waker-Stauffer. In addition, the spring 32 is preferably chosen such that the support structure does not elongate for stretching forces less than about one-half pound, and that the entire catheter elongates at a rate of about one inch for each one-half pound of force in excess of one-half pound.

Figures 6, 7, 8, 9:
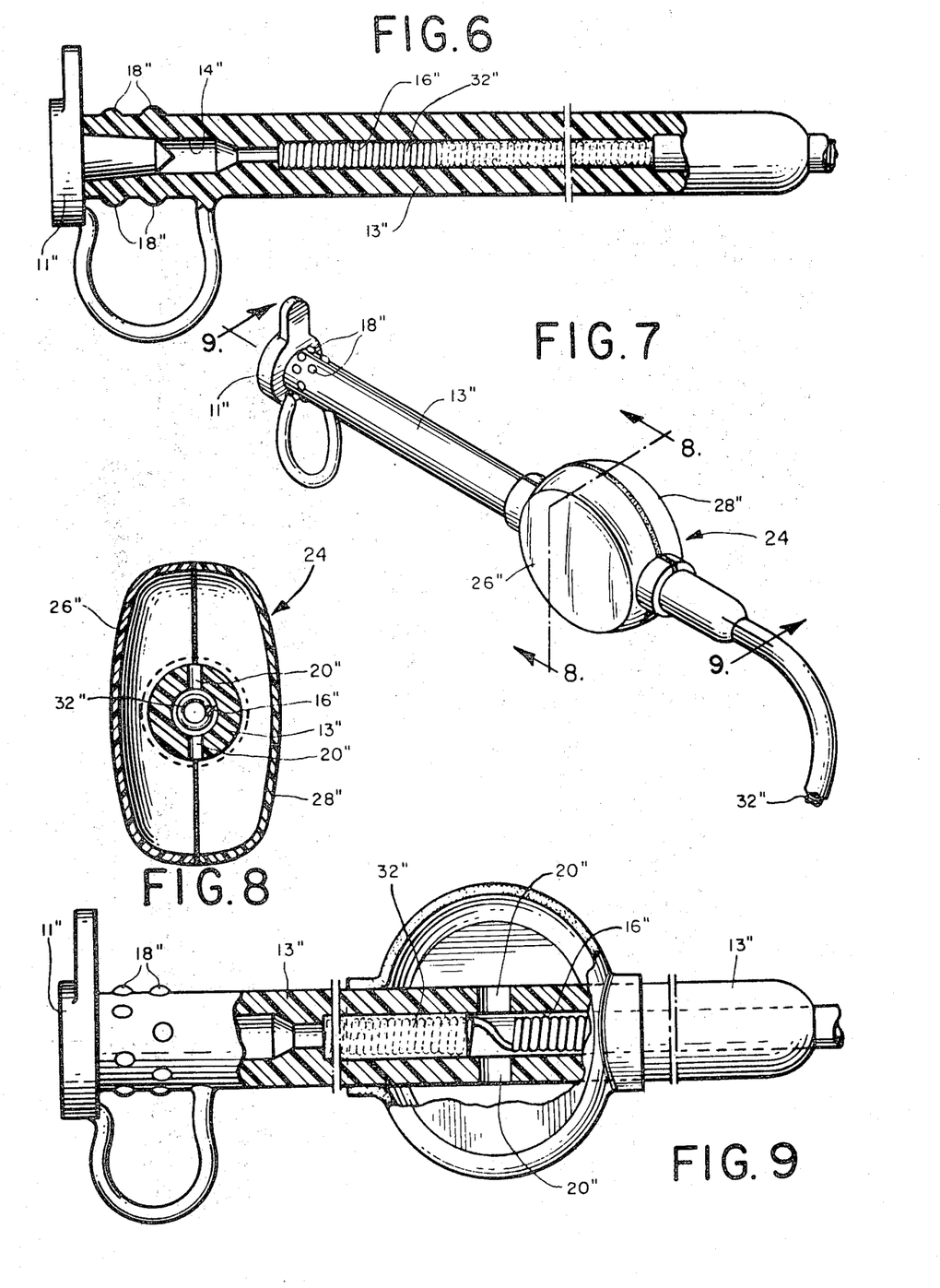
FIG. 6 is a partial sectional view of a second preferred embodiment showing an alternate construction for the proximal portion of the catheter of this invention.
FIG. 7 is a perspective view of the proximal end of a third preferred embodiment of the catheter of this invention.
FIG. 8 is a sectional view taken along line 8—8 of FIG. 7.
FIG. 9 is a sectional view taken along line 9—9 of FIG. 7.

FIG. 6 shows a portion of a second preferred embodiment of the catheter of this invention. This second preferred embodiment is identical to the embodiment of FIG. 1 except for the portion shown in FIG. 6, which includes a modified support tube 13". This support tube 13" is preferably formed of an elastomeric material such as silicone rubber, and it defines a spring receiving bore 16" and a syringe receiving bore 14". The syringe receiving bore 14" is sized to receive the projecting end of a syringe, and a cap 11" is molded to the tube 13" for sealing the bore 14" during storage. Preferably, a plurality of raised bumps 18" are molded in the tube 13" to engage the projecting end of a syringe (not shown). Helical or circumferential ridges could be substituted for the bumps 18". The spring 32" is securely bonded to the tube 13" in the spring receiving bore 16" by means of a suitable adhesive or the like.

This second preferred embodiment eliminates the need for metal luers such as the luer 12 of FIG. 2. In some applications, this may reduce manufacturing costs.

FIGS. 7, 8 and 9 show a portion of a third preferred embodiment of the invention. This third preferred embodiment is identical to that of FIG. 6 with the following exceptions. The tube 13" includes a pair of opposed openings 20" which extend from the outside of the tube 13" to the interior of the spring receiving bore 16". The spring 32" is provided with a spread portion 22" adjacent these opening 20" to allow fluid to flow from the openings 20" into the lumen of the spring 32". A chamber 24" is disposed around the tube 13" adjacent the openings 20". Preferably, this chamber 24" is formed of two symmetrical halves 26", 28" which are bonded to each other and to the tube 13" such that the chamber 24" is fluid tight and fluid can only enter or escape from the chamber 24" via the openings 20". Preferably the chamber 24" is formed of flexible material which has a low extensability, such that pressure variations of the fluid within the chamber 24" can readily be sensed by finger pressure on the outer walls of the chamber 24".

Preferably the chamber 24" is made of silicone rubber having a durometer in the range of 50-75.

The chamber 24" should have a rest state which defines a volume adequate to receive enough fluid from the balloon to totally deflate the balloon. This volume should be large enough that finger pressure on the chamber 24" can be used to inflate the balloon to the maximum extent necessary.

Figures 13, 14:
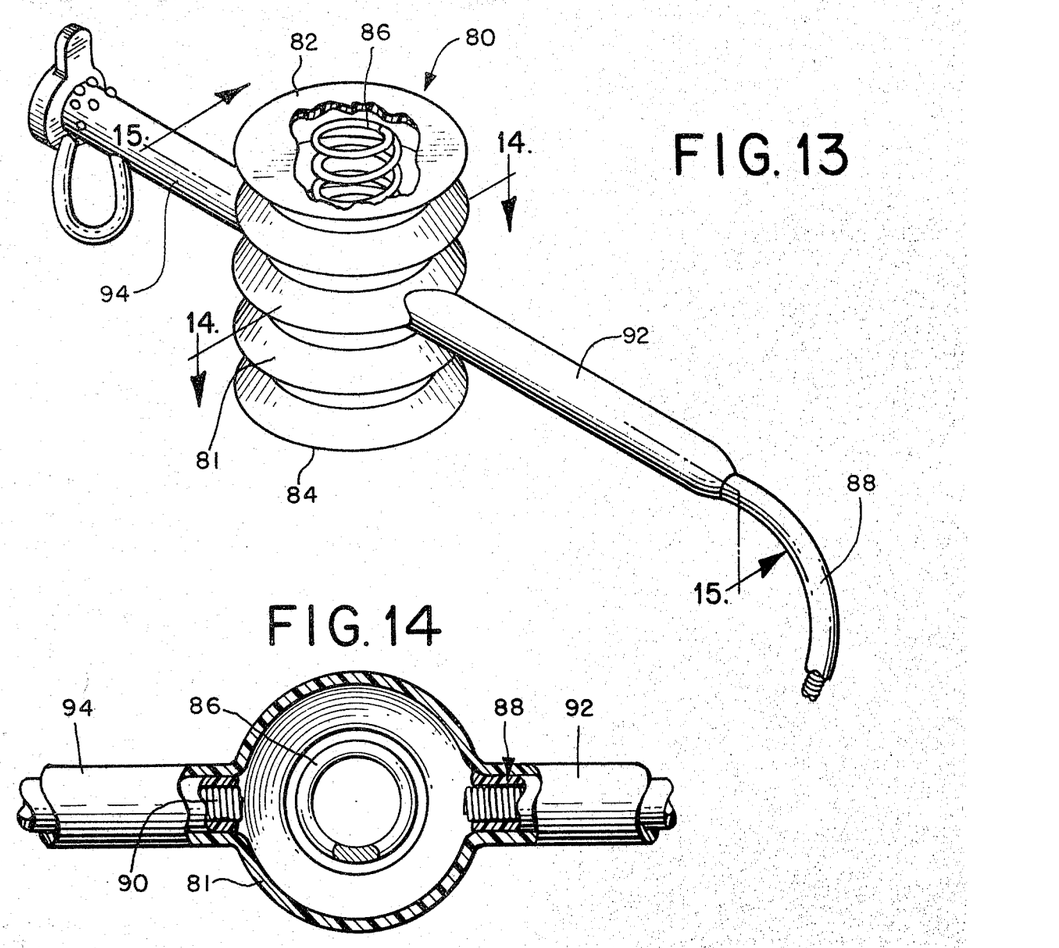
FIG. 13 is a perspective view of the proximal end of a fifth preferred embodiment of this invention.
FIG. 14 is a sectional view taken along line 14—14 of FIG. 13.
Figure 15:
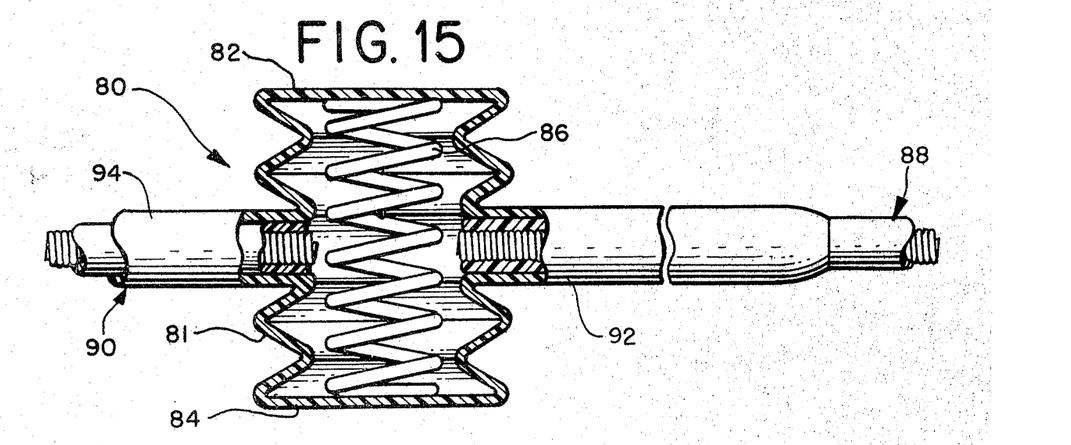
FIG. 15 is a sectional view taken along line 15—15 of FIG. 13.

FIGS. 13, 14 and 15 show the proximal portion of another embodiment of this invention which defines a chamber similar to that of the embodiment of FIGS. 7-9. The embodiment of FIGS. 13-15 differs from that of FIGS. 7-9 only in the structure of the chamber, and therefore only the chamber 80 will be described in detail.

Referring to FIG. 13, the chamber 80 is made up of a pleated, cylindrical side wall 81, a circular upper wall 82 and a circular lower wall 84. The chamber 80 also includes a coil spring 86 which extends between the upper and lower walls 82,84 within the side wall 81. The chamber 80 is in fluid communication with a balloon, not shown, by means of the catheter 88, and with a syringe receiving bore, not shown, similar to the bore 14" of FIG. 6, by means of the conduit 90. Reinforcing tubes 92,94 are bonded to respective portions of the side wall 81 to seal the catheter 88 and the conduit 90 to the chamber 80.

The upper and lower walls 82,84 in this preferred embodiment are about one inch apart, and each is about seven-eighths of an inch in diameter. Thus, the chamber 80 is sized to fit between the thumb and opposed forefinger of a user. Preferably, the user positions the pad of his thumb on either the upper or lower wall 82,84, and both the upper and lower walls 82,84 are formed of a thin sheet of a flexible but substantially inextensible material such as a suitable silicone rubber. Preferably the thickness of the upper and lower walls 82,84 is no greater than about 0.015 inches. It has been found that improved tactile sensing of pressure variations within the chamber 80 is possible when the walls 82,84 are thin and flexible. This allows the user to gauge precisely pressure variations inside the chamber 80, and thereby to avoid excessive pressures.

The chamber 80 should have a rest state which defines a volume adequate to receive enough fluid from the balloon to deflate the balloon completely. This volume should be large enough that finger pressure on the end walls 82,84 can be used to inflate the balloon to the maximum extent necessary.

Having described the structure of the presently preferred embodiments, the various safety features of the balloon catheter of this invention can now be described. As shown in FIG. 4, when the balloon catheter 10 is normally inflated, the balloon 50 is pushed away from the spring 32 by fluid which passes through the lumen of the coil spring 32 out the spread section 38 into the interior of the balloon 50. Normally, both the strain relief collar 60 and the secured section 62 of the bonding region 54, as well as the bonding region 56, remain against the spring 32. Once the balloon 50 has been inflated as shown in FIG. 4, it is then pulled through a body passage to remove material such as blood clots.

FIG. 5 shows a configuration of the balloon catheter 10 when excessive fluid pressure and over distension is developed within the balloon 50. Typically, this occurs when pulling forces are applied to the catheter in drawing the balloon 50 through a body passage. Under these conditions the balloon 50, when pulled, tends to elongate to form a pear shape and to pull back towards the distal end of the spring 32. Because the balloon 50 is formed of silicone rubber it is capable of elongating in this way in order to reduce the contact area between the balloon 50 and the inner walls of the body passage and therefore the total applied force. When the strain on the balloon 50 and the fluid pressure within the balloon 50 become excessive, the bonding region 54 is designed such that the strain relief collar 60 extends away from the coil spring 32. This extension provides two important safety advantages. First, when the collar 60 extends it effectively increases the volume of the balloon 50, because it temporarily receives and stores a portion of the fluid contained in the balloon 50. This of course tends to reduce the pressure applied to the body passage. In addition, when the strain relief collar 60 extends as shown in FIG. 5, it in effect lengthens the balloon 50 and reduces the strain placed on the bond between the proximal end of the balloon 50 and the strain relief collar 60 as well as the strain on the balloon 50. By relieving strain in this area, the life of the bond between the strain relief collar and the balloon 50 as well as the life of the balloon are increased. Thus, the strain relief collar 60 serves both to reduce pressure on the body passage under conditions of unusually high fluid pressure and to extend the life of the balloon 50.

FIGS. 4 and 5 illustrate a second important safety feature of the balloon catheter 10. As previously mentioned, the support structure 30, which in this preferred embodiment is about 35 inches long, includes a coil spring 32 and a sheath 42. In its rest state, as shown in FIG. 4, the coil spring 32 is a closely wound spring in which adjacent coils are in contact. However, both the spring 32 and the sheath 42 are extendable when sufficient stretching force is applied to the catheter. FIG. 5 shows a configuration of the support structure 30 when an excessive stretching force is applied, thereby causing adjacent coils of the coil spring 32 to separate. The spring 32 is preferably chosen such that for stretching forces below a threshold value the coils of the spring 32 remain adjacent one another. Thus, when a user exerts light or moderate pulling force in withdrawing the inflated balloon through a body passage, the support structure 32 remains substantially inextensible. Any minor extension of the support structure 30 is imperceptible to the physician, and the support structure 30 appears to have a fixed length.

However, when excessive stretching forces are applied, the coils of the spring 32 will spread as shown in FIG. 5. This extension of the support structure 30 provides several important advantages. First, it provides a tactile signal to the user that an excessive stretching force is being applied. This provides an immediate indication to the user that the stretching force and/or balloon distension should be reduced in order to prevent damage to the body passage. Second, the elongation of the support structure 30 tends to reduce the stretching force applied to the balloon 50 as it is being withdrawn from the body passage. Third, when the support structure 30 elongates, the volume of the support structure 30 increases. In this embodiment, this is because the coil spring 32 prevents the sheath 42 from reducing its internal diameter substantially as the coil spring 32 elongates. This increase in internal volume of the support structure 30 tends to decrease the volume of the balloon 50 when an excessive stretching force is applied to the luer 12. Thus, the support structure 30 of this preferred embodiment simultaneously removes fluid from the balloon to reduce balloon pressure, and provides tactile feedback to the physician when an excessive stretching force is applied. In this way, the danger of rupturing the body passage or of producing severe intimal damage to the body passage is reduced.

An additional important advantage of the embodiments of FIGS. 7-9 and 13-15 relates to the chambers 24",80. In use, a syringe is used to fill the interior volume of the deflated balloon, the support structure, the chamber 24",80, and the tube 13", and then the cap 11" is used to seal the tube 13". Then, when it is desired to inflate the balloon, finger pressure is applied directly to the chamber 24",80 by pressing the chamber 24",80 between the thumb and an opposed finger of the user.

The use of the chamber 24",80 instead of a syringe to inflate the balloon provides several important advantages. First, the chamber 24",80 allows the user to control the inflation pressure precisely and directly, much more precisely than is possible when a syringe is used to inflate the balloon. In this way the chance of over-inflation of the balloon is reduced. Preferably the volume of the chamber 24",80 is small enough that the free balloon cannot be burst by finger pressure on the chamber 24",80.

Second, the chamber 24",80 provides the user with a direct, tactile information as to the fluid pressure in the balloon. This information allows the user to directly feel when balloon pressure increases as the balloon is pulled through a body passage. The user can quickly and instinctively react to excessive pressure by relaxing the pressure he applies with his fingers to the chamber 24",80 thereby reducing balloon pressure. In this way the ever present danger of applying damaging forces to the body passage is further reduced.

The solder bond 40 is placed adjacent the proximal end of the balloon 50 in order to isolate the bonding region 54 from this elongation of the coil spring 32. This improves the reliability and increases the life of the bonding region 54.

The balloon catheter 10 of these preferred embodiments provides a number of significant advantages. Because the sheath 42 is formed of silicone rubber it is soft and flexible. The coil spring 32 provides memory allowing the catheter to assume its original configuration after storage and use, and the silicone rubber sheath 42 does not soften at body temperature.

Furthermore, silicone rubber is relatively inert, and because of the coil spring 32 the entire catheter is radiopaque. The smooth molded tip section 52 can be used either for embolectomy or thrombectomy procedures. Furthermore, in that the balloon 50 is formed of silicone rubber, it is softer and more conformable than latex rubber balloons of the prior art. These features of the balloon 50 allow it to assume the contour of the body passage at lower contact pressures. Therefore, reduced contact pressures are required to conform the balloon to the body passage and lower pressure is transmitted to the body passage wall. Furthermore, because of the softness and compliancy of the balloon 50, it will extend longitudinally and assume a somewhat pear shape configuration when excessive withdrawal forces are applied. This further reduces balloon contact area and significantly reduces the shear stress on the passage wall. This longitudinal extension further limits radial pressure of the balloon on the body passage, reducing the possibility of rupturing or otherwise severely damaging the body passage. Because the balloon is directly bonded to the catheter and becomes an integral part of the catheter, there are no ties that can become separated from the catheter and lost. Furthermore, silicone rubber tends not to fragment if ruptured and therefore there is a reduced danger of balloon fragments becoming lost within the body passage.

The coil spring 32 provides longitudinal rigidity and radial support to the catheter. As described above, its extensibility also provides a tactile signal to the user as well as a reduction in the stretching forces applied to the balloon and a reduction in the volume of the balloon when necessary. The catheter can be packaged in a coiled position and placed within a small package for storage. No special conditions are necessary for storage, and if the catheter is taken out of its sterile package but not used it can be resterilized using steam or ethylene oxide gas.

Of course, it will be apparent to those skilled in the art that various changes and modifications to the preferred embodiment described above can be made without departing from the spirit and scope of the present invention. For example, in some embodiments it may be advantageous to extrude the silicone rubber sheath over the coil spring to fabricate the support structure. In addition, other elongatable support structures can be used to provide the tactile signal of excessive stretching force, and other types of means for receiving and storing fluid from the balloon when fluid pressure within the balloon exceeds a predetermined value can be used.

Figure 10A:
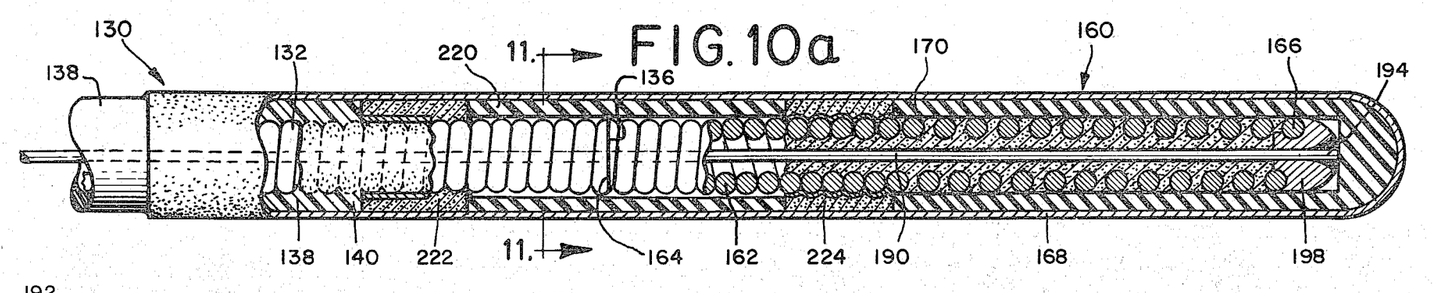
FIG. 10a is a partial sectional view of the distal or tip portion of a fourth preferred embodiment of the catheter of this invention, showing the balloon member deflated.

Turning now to FIGS. 10a-12b, the fourth preferred embodiment there illustrated provides a number of novel features which cooperate to provide a balloon member which inflates concentrically about the catheter as well as an important degree of protection against the development of excessive pressures inside the balloon of this catheter. FIGS. 10a and 10b show cross-sectional views of portions of this fourth preferred embodiment showing the arrangement of component parts when the balloon is deflated. As shown in FIG. 10a this embodiment includes a proximal catheter segment 130, a distal catheter segment 160, and a balloon member 220 which is disposed between the proximal and distal catheter segments 130,160.

Figures 10B, 11:
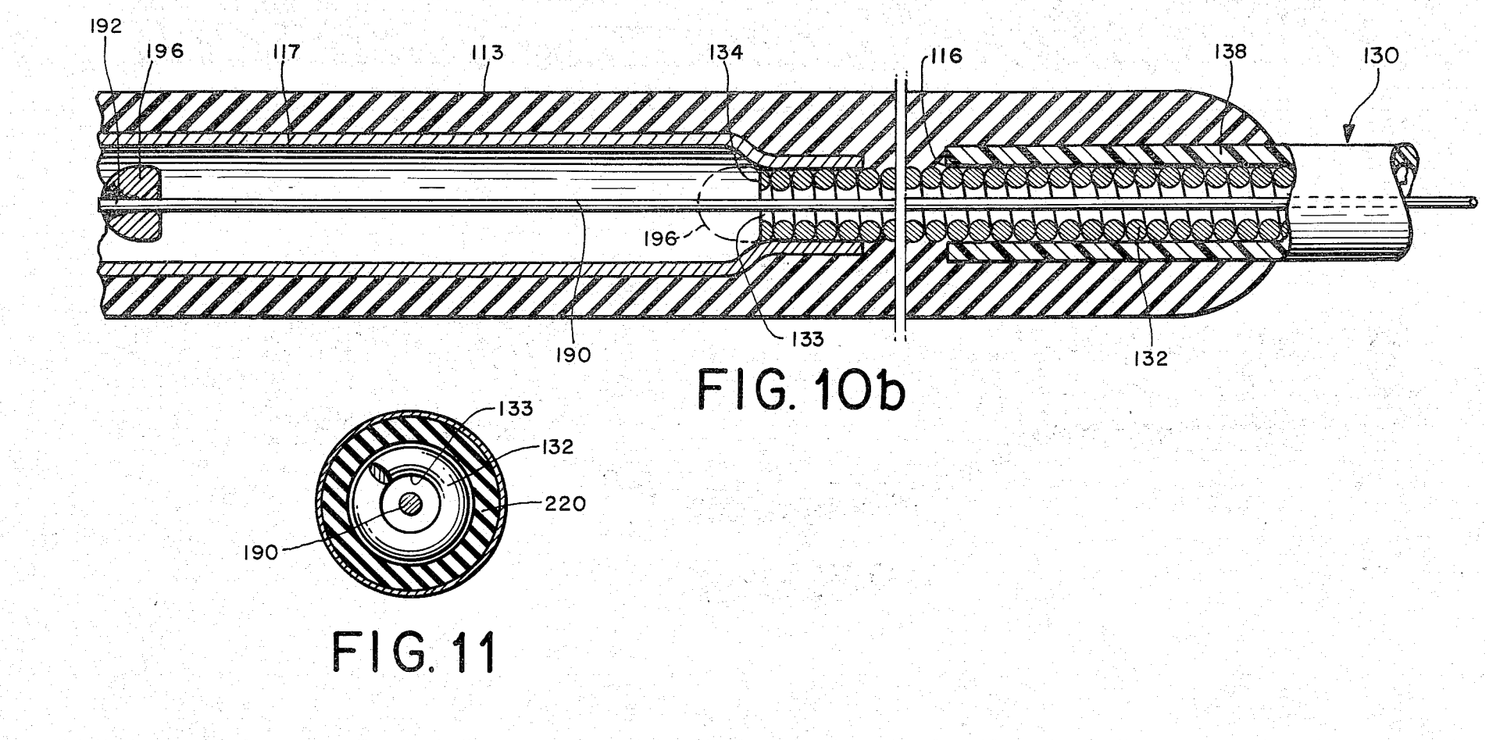

The proximal catheter segment 130 includes a proximal coil spring 132 which defines an internal lumen 133. This proximal coil spring 132 terminates distally at a distal end 136. The major portion of the proximal coil spring 132 is surrounded by a flexible, fluid impermeable proximal sheath 138 which terminates distally at a distal end 140. The distal catheter segment 160 includes a distal coil spring 162 which is provided with a proximal end 164 and a distal end 166. The major portion of the distal coil spring 162 is surrounded by a distal sheath 168, which terminates proximally in a proximal end 170. The balloon member 220 is bonded at one end by means of a bonding sleeve 222 to the distal end 140 of the proximal sheath 138. The other end of the balloon member 220 is bonded by means of the bonding sleeve 224 to the proximal end 170 of the distal sheath 168.

With certain exceptions to be noted below, the coil springs 132,162, the sheaths 138,168, the balloon member 220 and the bonding sleeves 222,224 are identical to the corresponding components illustrated in FIG. 3 and discussed above. These components will therefore not be described in detail here.

Among the important differences between the catheter of FIGS. 10a,10b and that of FIG. 3 is that the proximal coil spring 132 is severed from the distal coil spring 162 such that the distal end 136 of the proximal coil spring 132 is in an abutting relationship with the proximal end 164 of the distal coil spring 162. In the uninflated state it is the resilience of the balloon member 220 which urges the distal coil spring 162 against the proximal coil spring 132, as shown in FIG. 10a. In addition, the catheter of FIG. 10a is provided with a tension member such as a wire 190 which defines a distal end 194 which is securely fastened to a retaining member 198. This wire 190 extends down the lumen of both the distal and proximal coil springs 162, 132. The distal end 194 of the wire 190 is securely attached to the distal catheter segment 160 as, for example, by welding or silver soldering the distal end 194 to the retaining member 198. However, the wire 190 is free to slide in the lumen 133 of the proximal coil spring 132. In this preferred embodiment, the wire 190 is round in cross-section and has a diameter of about 0.006 inches. This wire should be formed of a material with high tensile strength and adequate flexibility, such as 302 or 316 stainless steel, for example. This wire is particularly suitable for a number four catheter of the type described above having coil springs 132,162 with an outside diameter of about 0.040 inches and a lumen 133 of about 0.018 inches. Of course, it should be understood that these dimensions can be altered as desired to form catheters of sizes other than the illustrated catheter described above.

Turning now to FIG. 10b, the proximal catheter segment 130 terminates in a support tube 113 which is securely fastened to the proximal end of the proximal catheter segment 130. This support tube 113, which is preferably formed of a flexible elastomeric material, defines a syringe receiving bore (not shown) which is in fluid communication with a spring receiving bore 116. Preferably, a cap (not shown) is provided to seal the syringe receiving bore. With the exceptions to be discussed below, this support tube 113 is substantially identical to the support tube 13" of FIG. 6.

Among the important differences between the support tube 113 of FIG. 10b and previously described embodiments is that the support tube 113 includes a cylindrical hollow sleeve 117 which is mounted to the proximal end 134 of the proximal coil spring 132. This sleeve 117 is substantially rigid and it serves as a guide for a stop member 196 which is rigidly secured, as by welding or silver soldering, for example, to the proximal end 192 of the wire 190. The diameter of the stop member 196 is larger than that of the lumen 133, such that the stop member 196 is prevented from passing into the lumen 133. Thus, the stop member 196 cooperates with the proximal end 134 of the proximal coil spring 132, which serves in effect as a second stop member, thereby limiting the sliding movement of the wire 190 in the proximal coil spring 132. The inner diameter of the sleeve 117 should be large enough to permit an adequate flow rate of fluid within the sleeve 117 past the stop member 196. FIG. 10b shows an illustrative position of the stop member 196 when the balloon member 220 is in its deflated state, as shown in FIG. 10a. In this preferred embodiment a separation of about ⅜ of an inch is provided between the stop member 196 and the proximal end 134 of the proximal coil spring 132. Thus, in this preferred embodiment the wire 190 is allowed to slide axially within the lumen 133 by a maximum amount of about ⅜ of an inch.

Figure 12A:
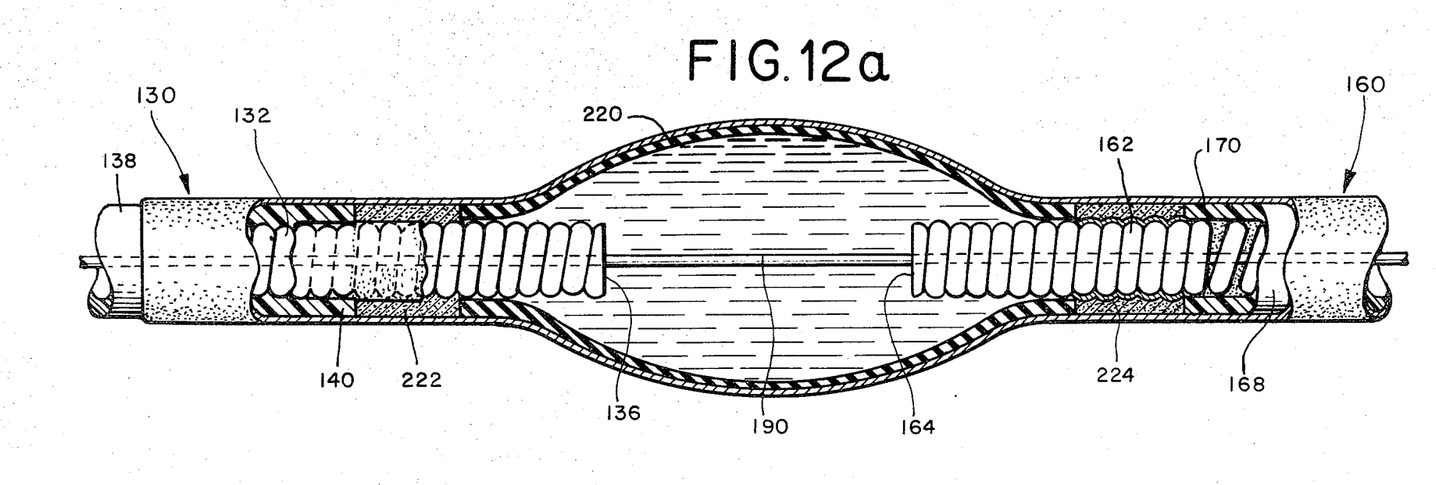
FIG. 12a is a partial sectional view corresponding to FIG. 10a showing the position of component parts of the tip portion of the catheter of FIG. 10a when the balloon is in a normally inflated state.
Figure 12B:
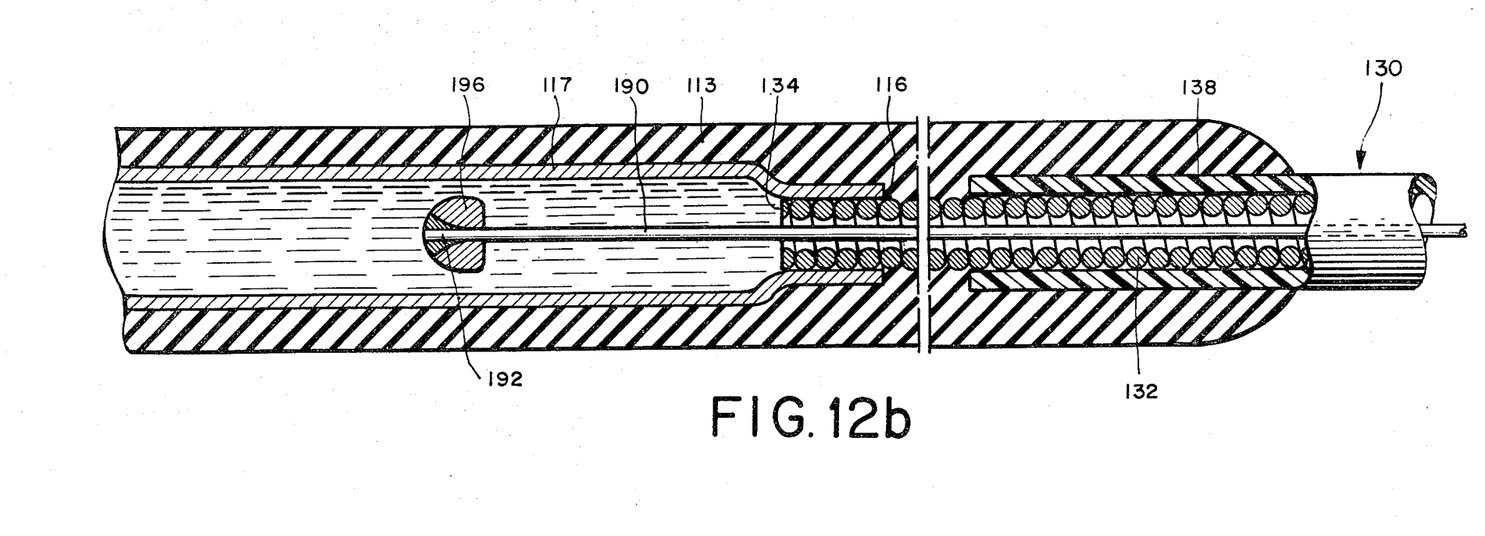

FIGS. 12a and 12b correspond with FIGS. 10a,10b, respectively, except that in FIGS. 12a and 12b the catheter of this embodiment is shown with the balloon member 220 inflated. As can be seen clearly in FIG. 12a, as the balloon member 220 inflates it stretches both circumferentially, to allow for the increased diameter of the balloon member 220, as well as axially. An important part of the axial stretching of the balloon member 220 is the result of the separation between the distal end 136 of the proximal coil spring 132, on the one hand, and the proximal end 164 of the distal coil spring 162, on the other hand. Thus, the novel structure of this embodiment allows the balloon member 220 automatically to stretch both axially and circumferentially as it inflates.

Normally, when the balloon member 220 is inflated for use, the stop member 196 will still be some distance from the proximal end 134 of the proximal coil spring 132, as shown in FIG. 12b. In this position, the catheter of this invention will allow the balloon member 220 to stretch further in the axial direction if excessive pressures are applied to the balloon member 220. Thus, for example, if the inflated balloon member 220 encounters a restriction in a body passage as it is being pulled through the body passage, such a restriction will cause increased pressure inside the balloon member 220. This increased pressure will operate automatically to elongate the balloon member 220 and to cause the wire 190 to slide in the lumen 133, thereby bringing the stop member 196 closer to the proximal end 134 of the proximal coil spring 132. In this way, excessive pressure inside the balloon member 220 acts to elongate the balloon member 220 automatically, thereby reducing pressure in the balloon member 220, as well as damage to the restricted portion of the body passage. Thus, this fourth preferred embodiment provides means for automatically reducing the diameter of the balloon member 220 when excessive pressures are developed therein.

From the foregoing discussion it should be apparent that an improved balloon catheter has been described which exhibits both improved concentricity of the balloon defined by the balloon member 220, as well as an important degree of protection for body tissues against overpressure. Another important advantage of this fourth embodiment is that, even though the proximal catheter segment is connected to the distal catheter segment only by the wire 190 and the balloon member 220, the distal catheter segment 160 is still securely held in place. Thus, the chance that the distal catheter segment 160 might break away and be lost in the body passage is remote.

It should be understood that the novel features of this fourth embodiment are not limited to the structure shown in FIGS. 10-12. For example, a rectangular wire may be substituted for the cylindrical wire 190 discussed above. It has been found that a rectangular wire having a cross-section of 0.003 inches by 0.008 inches provides good flexibility. Preferably, this rectangular wire is secured at a point near the distal end of the proximal coil spring to a less flexible, round wire which passes through the balloon member and is secured to the distal catheter segment. In addition, it is not necessary in all embodiments that the wire 190 be secured to the distal catheter segment 160 and be free to slide in the proximal catheter segment 130. For example, in alternate embodiments it may be preferable to secure the wire 190 to the proximal catheter segment 130 and to allow the wire 190 to slide within the distal catheter segment 160. In addition, in some embodiments it may be preferable to bond one end of the wire 190 to the proximal catheter segment and the other end of the wire 190 to the distal catheter segment, while providing the wire 190 with adequate length to permit the balloon member 220 to stretch axially as discussed above without stretching beyond a predetermined limit. For example, the extra length of the wire 190 can be formed as a light coil spring which causes the extra length of wire to coil between the proximal and distal springs 132,162 when the balloon member 220 is deflated, without substantially interfering with inflation of the balloon member as discussed above. Furthermore, it may be possible to dispense with the sleeve 117 in embodiments which utilize a rigid support tube 113. Moreover, other support structures may be substituted for the coil springs in some embodiments, and in some applications it may be preferable to inflate the balloon member 220 to the point where the stop member 196 normally abuts the second stop member.

Other resilient materials in addition to silicone rubber, such as low durometer urethane or latex, for example, can be used in some embodiments. These and other changes and modifications can be made without departing from the true spirit and scope of the present invention. It is therefore intended that all such changes and modifications be covered by the following claims.

We claim:

1. A balloon catheter for insertion in a body passage, said catheter comprising:
 a proximal cathether segment comprising a proximal coil spring disposed inside a proximal sheath that is sized to fit within the body passage;
 a distal catheter segment comprising a distal coil spring disposed inside a distal sheath that is sized to fit within the body passage;
 the proximal and distal coil springs being movable apart under pressure of fluid introduced through the lumen of the proximal coil spring;
 an inflatable resilient balloon member secured to and disposed between the proximal and distal catheter segments and sized to fit within the body passage, the balloon member having a proximal end secured to the proximal sheath and a distal end secured to the distal sheath, such that fluid introduced into the lumen of the proximal coil spring is confined within a volume bounded by the balloon member and the proximal and distal sheaths; and
 means for coupling the proximal catheter segment to the distal catheter segment such that the separation therebetween and therefore the length of the balloon member in the direction of the catheter increases automatically as the balloon member inflates, yet the separation therebetween is prevented from exceeding a maximum value.

2. A balloon catheter for insertion in a body passage, said catheter comprising:
 a proximal catheter segment comprising a proximal coil spring disposed inside a proximal sheath that is sized to fit within the body passage;
 a distal catheter segment comprising a distal coil spring disposed inside a distal sheath that is sized to fit within the body passage;
 the proximal and distal coil springs being movable apart under pressure of fluid introduced through the lumen of the proximal coil spring;
 an inflatale resilient balloon member secured to and disposed between the proximal and distal catheter segments and sized to fit within the body passage, the balloon member having a proximal end secured to the proximal sheath and a distal end secured to the distal sheath, such that fluid introduced into the lumen of the proximal coil spring is confined within a volume bounded by the balloon member and the proximal and distal sheaths; and
 means for coupling the proximal catheter segment to the distal catheter segment such that the separation therebetween and therefore the length of the balloon member in the direction of the catheter increase automatically in response to an external pressure applied to the inflated balloon member, yet the separation therebetween is prevented from exceeding a maximum value.

3. The invention of claim 1 or 2 wherein the coupling means comprises:
 an elongated tension member disposed to slide within one of the proximal and distal catheter segments and secured to the other of the proximal and distal catheter segments; and
 means for limiting the sliding motion of the tension member in said one catheter segment.

4. The invention of claim 1 or 2 wherein the coupling means comprises:
 an elongated tension member disposed to slide within the proximal coil spring and secured to the distal catheter segment; and
 means for limiting the sliding motion of the tension member in the direction of the distal catheter segment.

5. The invention of claim 4 wherein the limiting means comprises:
 a first stop member secured to the tension member; and
 a second stop member, included in the proximal catheter segment and positioned to limit the movement of the first stop member in the direction of the distal catheter segment.

6. The invention of claim 5 wherein the second stop member is defined by the proximal end of the proximal coil spring.

7. The invention of claim 3 wherein only the tension member and the balloon member extend between the proximal and distal catheter segments.

8. A balloon catheter for insertion in a body passage, said catheter comprising:
 a proximal coil spring;
 a distal catheter segment, the distal catheter segment comprising a distal coil spring and a distal sheath disposed around the distal coil spring;
 the proximal and distal coil springs being movable apart under pressure of fluid introduced through the lumen of the proximal coil spring;
 an elongated tension member wire secured to the distal catheter segment and slidably disposed within the lumen of the proximal coil spring;
 a proximal sheath disposed around the proximal coil spring;
 an inflatable elastic balloon member positioned around the distal end of the proximal coil spring and secured between the proximal sheath and the distal catheter segment; and
 means for allowing limited sliding movement of said tension member with respect to the proximal coil spring in the direction of the distal catheter segment in order to allow the length of the elastic balloon member to vary automatically during inflation of the balloon member in the direction of the catheter while limiting the maximum separation between the proximal coil spring and the distal catheter segment.

9. The invention of claim 8 wherein the proximal end of the tension member extends beyond the proximal end of the proximal coil spring and the limiting means comprises a stop member secured to the proximal end of the tension member.

10. A balloon catheter for insertion in a body passage, said catheter comprising:
- a proximal coil spring having a proximal end and a distal end;
- a proximal sheath disposed around the proximal coil spring;
- a distal coil spring having a proximal end;
- a distal sheath disposed around the distal coil spring;
- an inflatable balloon member disposed around the distal end of the proximal coil spring and the proximal end of the distal coil spring and secured between the proximal and distal coil springs;
- the proximal and distal coil springs being movable apart under pressure of fluid introduced through the lumen of the proximal coil spring;
- a flexible wire secured to the distal coil spring and disposed to slide within the lumen of the proximal coil spring, said wire having a proximal end which extends beyond the proximal end of the proximal coil spring;
- a first stop member secured to the proximal end of the wire; and
- a second stop member fixedly mounted with respect to the proximal coil spring to engage the first stop member and thereby to limit the movement of the first stop member in the direction of the balloon member;
- said stop member positioned on said wire such that a predetermined length of the wire separates the first stop member from the second stop member when the balloon is deflated, thereby allowing a predetermined maximum separation between the distal end of the proximal coil spring and the proximal end of the distal coil spring when the balloon member is inflated.

* * * * *